United States Patent [19]

Jaffari et al.

[11] Patent Number: 4,835,309
[45] Date of Patent: May 30, 1989

[54] ION EXCHANGE RECOVERY OF L-LYSINE

[75] Inventors: Mark D. Jaffari, Leroy; Jeffrey T. Mahar; Richard L. Bachert, both of Rochester, all of N.Y.

[73] Assignee: Eastman Kodak Company, Rochester, N.Y.

[21] Appl. No.: 181,470

[22] Filed: Apr. 14, 1988

[51] Int. Cl.$^4$ .............................................. C07C 99/12
[52] U.S. Cl. ..................................... 562/554; 562/562
[58] Field of Search ................................ 562/554, 562

[56] References Cited

U.S. PATENT DOCUMENTS

| | | | |
|---|---|---|---|
| 3,565,951 | 2/1971 | Ishida et al. | 260/527 |
| 4,714,767 | 12/1987 | Tanaka et al. | 562/554 |

FOREIGN PATENT DOCUMENTS

| | | | |
|---|---|---|---|
| 595403 | 3/1960 | Canada | 562/554 |
| 595404 | 3/1960 | Canada | 562/554 |
| 666169 | 6/1979 | U.S.S.R. | 562/554 |
| 722904 | 3/1980 | U.S.S.R. | 562/562 |
| 804970 | 11/1958 | United Kingdom | 562/554 |
| 1178011 | 1/1970 | United Kingdom | 562/554 |

*Primary Examiner*—James H. Reamer
*Attorney, Agent, or Firm*—J. Jeffrey Hawley

[57] ABSTRACT

L-lysine is recovered using an ion exchange resin. A liquid solution containing L-lysine and possibly impurities is contacted with the resin and is then soaked in elutant for at least about 15 minutes. The elution of L-Lysine from the resin is then continued.

6 Claims, No Drawings

ION EXCHANGE RECOVERY OF L-LYSINE

BACKGROUND OF THE INVENTION

The present invention is directed to the recovery of L-lysine from a liquid solution using an ion exchange resin. The method produces L-lysine in high purity and yield. In a preferred method, a highly concentrated solution of L-lysine free base is produced which can be used directly as a feed supplement.

DESCRIPTION RELATIVE TO THE PRIOR ART

L-lysine is one of the essential amino acids. It is conveniently produced in commercial quantities by fermentation of L-lysine producing microorganisms. However, it is produced along with other materials and must therefore be recovered in a purified form from the solutions in which it is produced.

One of the common methods for the recovery of L-lysine is to use an ion exchange resin. In U.S. Pat. No. 3,565,951, for example, there is described a method wherein a fermentation broth is adjusted to a pH of between 0.5 and 3.0 before it is contacted with a strongly acidic cation exchange resin of the ammonium type. The resin is then eluted with ammonium hydroxide to recover the adsorbed L-lysine.

Very high purities of L-lysine HCl are reported in the disclosure of this patent. However, the final purity is influenced by the nature of the starting material, for example, the amount of lysine in the fermentation medium. While this process may have been adequate for the starting material used in the examples of this patent, it has been found that the purity and yield using this process has not been satisfactory for every starting solution containing L-lysine. Further, the high purity is only obtained after crystallization as the hydrochloride. There has thus been a need for an improved process which is capable of high purities and high yields of recovered L-lysine while at the same time producing a solution having a relatively high L-lysine concentration.

In addition, in the disclosure of the '951 patent, the product that is ultimately recovered is a dry form of L-lysine HCl. The elutant is acidified with hydrochloric acid to produce the L-lysine HCl. This is then precipitated and dried. This dry form requires additional process steps and reagents to produce.

SUMMARY OF THE INVENTION

In accordance with the present invention there is provided a method for the recovery of L-lysine from a liquid solution using a strongly cationic ion exchange resin, said method comprising the steps of (a) contacting said ion exchange resin with said liquid solution, then (b) washing said exchange resin to remove impurities, then (c) soaking said resin in an eluting solution for at least about 15 minutes and then (d) eluting said L-lysine from said resin with an eluting solution to form a solution containing recovered L-lysine.

In a preferred embodiment, the resin is saturated with L-lysine prior to the soaking step.

In accordance with another preferred embodiment of the invention, it is desired to prepare a L-lysine free base concentrated solution. Thus, there is provided the additional step of concentrating the eluate from step (d) such that the concentration of L-lysine free base is between about 500 and 775 g/L.

DETAILED DESCRIPTION OF THE INVENTION

The method of the invention includes a soak step that is not suggested in the '951 patent. This soak step provides improved results over the known methods. It produces an eluant which contains higher concentrations of L-lysine. The higher concentrations result in lower costs for any subsequent process steps.

In accordance with a preferred embodiment of the present invention, the ion exchange resin is saturated with L-lysine. In the '951 patent as in other patents relating to ion exchange recovery of amino acids, the ion exchange resin is not saturated. The ion exchange resin is typically in the form of a column that is "loaded" by passing the starting liquid containing the L-lysine into one end of the column and allowing it to exit the other. According to '951, loading is terminated when L-lysine just begins to appear at the other end of the column.

In contrast, in the preferred aspect of the present invention, the ion exchange resin is saturated. This is achieved when L-lysine in the solution is in equilibrium with the L-lysine that is adsorbed to the ion exchange resin. This is determined in a column for example, when the concentration of the L-lysine in the solution entering the column is the same as that exiting the column.

The method of the invention is useful in recovering L-lysine from any liquid solution. The most common solution is a fermentation broth that contains spent media, microbial cells, other amino acids and other impurities. Where the liquid does contain solids, for example microbial cells, these should be removed before the solution is contacted with the ion exchange resin.

Microbial cells can be removed by conventional methods. Useful methods include filtration, either continuous or batch, and centrifugation. It has been found that the cells filtered from the spent broth have some L-lysine associated therewith. Therefore, it is desirable to wash the filtrate cells with water and add the water to the supernatant for subsequent ion exchange recovery.

As is conventional, the solution after cell removal is adjusted to a pH of between about 0.5 and 3.0 with an acid solution, for example, sulfuric acid.

The acidified solution is then contacted with a conventional ion exchange resin. The resin can be contained in any suitable container but is usually in a column. The resin is of the strongly cationic type, for example, Dowex 50W-X8 NH4+ available from the Dow Chemical Company, Midland Mich. USA; Amberlite IR-120 available from Rohm and Haas Company Philadelphia Pa. USA or any equivalent resin.

As noted in detail above, in preferred embodiments the ion exchange resin is saturated with L-lysine. Initially, the resin will take up all of the L-lysine that is in the solution. Where a column is being used, the L-lysine free solution that exits the column can be discarded. When L-lysine begins to appear in the solution exiting the column, the exit stream can be recycled.

After contact with the L-lysine containing solution, the ion exchange resin is washed to remove impurities. Washing can be with water and the completion of the washing can be determined by observing the clarity of the wash solution. When the wash solution turns clear, impurities have been removed from the column.

The eluting solution that is used in the soak and eluting steps, is a basic solution that contains the cation of the original ion exchange resin. The specific resins mentioned above are both ammonium type ion exchange resins and the base is therefore preferably an ammonium salt. Ammonium hydroxide, ammonium carbonate or bicarbonate can be used. Particularly good results have been achieved using ammonium carbonate. Other bases such as alkali metal hydroxides can also be used. The pH of the elutant is typically between about 11 and 12.

The ion exchange resin is allowed to soak in the elutant for at least about 15 minutes and preferably 30 to 45 minutes. Elution is then continued until L-lysine is no longer noted in the elutant stream. The elutant collected after soaking contains the recovered purified L-lysine.

The L-lysine containing elutant can be further processed. The solution can be acidified, for example with hydrochloric acid to thereby form L-lysine/HCl. This salt precipitates and can be filtered off and dried.

In a preferred process, the elutant containing the recovered L-lysine free base is not acidified but is concentrated so as to produce a L-lysine free base concentrate that contains between about 500 and 775 g/L L-lysine free base. Higher concentrations tend to form a gel. This concentrate can be used directly, for example as an animal feed supplement.

The concentration of the elutant to produce the liquid L-lysine concentrate can be by conventional methods. Evaporation is one convenient method, however, other methods of removing water can also be used such as reverse osmosis.

The following examples are provided for a further understanding of the invention.

Examples 1–2

Example 2 is a comparative example.

Two lysine broth adsorption and elution experiments varying as outlined in Table I were performed to illustrate the practice of this invention.

TABLE I

| Experimental Variations in Adsorptive Lysine Recovery | |
|---|---|
| Example | Variation |
| 1 (Invention) | Saturated resin upon adsorption and soak for elution. |
| 2 (Comparative) | Saturated resin upon adsorption and no soaking during elution |

A filtered microbial fermentation broth containing 46.9 g lysine/liter was adjusted to a pH of 2 with sulfuric acid. Portions of this broth were used as feeds for all of the following adsorptive lysine recovery experiments. For each experiment columns were packed with Amberlite IR-120 strongly cationic ion exchange resin in the ammonium form. Amberlite ion exchange resins are sold by Rohm and Haas Corporation. The dimensions of the packed columns were 2.5 cm diameter by 20 cm resin height. Fresh resin was used for each experiment. The broth was pumped through the columns to provide a downflow of about 4 mL/min at 20° C. in each of the experiments. The final effluent concentrations in Examples 1 and 2 were equal to the feed concentrations, thus saturating each column after 800 mL of broth was pumped into each column. Pumping was stopped when the effluent concentration of 0.1 g of lysine/liter was reached.

After this adsorption step each column was backflushed with deionized water for 10 hours to remove the unadsorbed, interstitial material. The elutions were performed after the backflushing. The eluant for the three experiments was 2N ammonium hydroxide at a pH of 12.

The eluant for Example 1 was pumped into the column at 20° C. and 15 mL/minute for 6.5 minutes for a total of 97.5 mL. The flow was stopped and the effluent concentration just prior to stopping was 0.5 g lysine/liter. The column was allowed to stand and soak for 30 minutes before resuming flow at 15 mL/minute. Flow was continued for 91.5 additional minutes for a total of 98 minutes of flow and 1012.5 mL of broth. The final effluent concentration was 0.1 g of lysine/liter.

The same elution conditions were used for comparative Example 2 but no soaking was done. A total of 1020 mL of eluant were pumped into the column and the final effluent concentration was 0.1 g of lysine/liter.

The concentration of L-lysine was measured in the eluant stream. The peak concentration and the average concentration for the collected eluant (based on 96% recovery) is given in Table II (lysine concentration g/L). The eluant stream from each experiment was then concentrated to dryness and analyzed for the weight percent of lysine present in the residue (lysine purity). The results are also reported in Table II.

TABLE II

| Example | Lysine Purity | Lysine Concentration | |
|---|---|---|---|
| | | Peak | Average |
| 1 | 90.7 | 92.2 | 34.6 |
| 2 | 87.8 | 74.7 | 29.9 |

Example 3

A cell-free fermentation broth of 12.9 liters, which contained 33.7 g/L L-lysine free base per liter at a 46.5% L-lysine purity, was adjusted to a pH of 2 with sulfuric acid. The solution was then passed over a column containing 6 liters of a strongly cationic resin (Dowex 50W-X8 $NH_4+$). This represents more than enough resin to absorb all of the lysine in the solution. The column was back-washed with distilled water until the overflow was clear. The resin was initially soaked with a 2N ammonium hydroxide solution for 30 minutes and then continued to be eluted with 4 bed volumes (24 liters) of the ammonium hydroxide solution. The concentration of the L-lysine in the collected eluate was 16.7 g/L. The eluate was concentrated to 2.51 liters by using a reverse osmosis plate and frame DDS Lab Unit 20 with DDA HR-98 membranes at $43. \times 10^6$ Pa and 25° C. Retentate in the amount of 200 mL was further concentrated to 43 mL using a Buchi Rotavapor at 50° C. and under about 100 cm of Hg. Approximately 94.3% of the L-lysine was recovered at a concentration of 742 g L-lysine free base/L (601 g L-lysine free base/Kg) and a purity of 95.1%.

Example 4

A fed-batch fermentation produced 2.3 liters of 48.2 grams L-lysine free base per liter at a 48.7% purity. The microbial cells were separated from the broth by ultrafiltration using a plate and frame DDS Lab Unit 20 with polyethersulfone membranes having a molecular weight cut-off of 100K. There was no washing of the microbial cells. The L-lysine purity of the permeate after cell removal increased to 67.1%. The pH of the permeate was adjusted to 2 with sulfuric acid. Permeate of 1.74 liters were passed over a column containing 5 liters of a strongly cationic resin (Dowex 50W-X8 NH$_4$+). The column was backwashed with distilled water until the overflow was clear. The resin was initially soaked with a 2N ammonium hydroxide solution for 30 minutes and then continued to be eluted with 1.77 liters of the ammonium hydroxide solution. The concentration of L-lysine in the collected eluate was 28.4 g/L. The ion exchange eluate was concentrated to 67 ml using a Buchi Rotavapor at 45°–50° C. under 76–102 cm of Hg. The concentration and purity of the liquid lysine product was 750 g L-lysine free base/l (600 g L-lysine free base/Kg) and 97.2%, respectively. The product form was stable for over 23 days.

Example 5

A fed-batch fermentation produced 2.0 liters of 48.2 grams L-lysine free base per liter at a 48.7% purity. The microbial cells were separated from the broth by centrifugation using a Superspeed Sorvall at 8000 RPM for 40 minutes at 30° C. There was no washing of the microbial cells. The purity of the permeate after cell removal increased to 62.4%. The pH of the permeate was adjusted to 2 with sulfuric acid.permeate in the amount of 1.54 liters were passed over a column containing 5 liters of a strongly cationic resin (Dowex 50W-X8 NH$_4$+). The column was backwashed with distilled water until the overflow was clear. The resin was initially soaked with a 2N ammonium hydroxide solution for a half hour and then continued to be eluted with 1.55 liters of the ammonium hydroxide solution. The concentration of L-lysine in the collected eluate was 41.6 g/L. The ion exchange eluate was concentrated to 83 ml using a Buchi Rotavapor at 45°–50° C. under about 75–100 cm of Hg. The concentration and purity of the liquid lysine product was 777 g L-lysine free base/L (624 g L-lysine free base/Kg) and 99.4%, respectively. The liquid lysine product had a viscosity of 0.213 Pa-second and was stable for over 23 days.

The invention has been described in detail with particular reference to preferred embodiments thereof, but it will be understood that variations and modifications can be effected within the spirit and scope of the invention.

What is claimed is:

1. A method for the recovery of L-lysine from a liquid solution using a strongly cationic ion exchange resin, said method comprising the steps of
    (a) contacting said ion exchange resin with said liquid solution, then
    (b) washing said exchange resin to remove impurities, then
    (c) soaking said resin in an eluting solution for at least about 15 minutes and then
    (d) eluting said L-lysine from said resin with an eluting solution to form a solution containing recovered L-lysine.

2. A method according to claim 1 wherein said resin is saturated with L-lysine.

3. A method according to claim 1 comprising the additional step of concentrating the eluate from step (d) such that the concentration of L-lysine free base is between about 500 and 775 g/L.

4. A method according to claim 1 wherein said eluting solution is ammonium carbonate.

5. A method according to claim 1 wherein said soaking step (c) is carried out for at least about 30 minutes.

6. A method for the recovery of L-lysine from a fermentation broth using a strongly cationic ion exchange resin, said method comprising the steps of:
    (a) separating the microbial cells from said broth leaving a L-lysine containing liquid solution,
    (b) washing said separated cells with wash water and adding said wash water to said L-lysine containing liquid solution, then
    (c) contacting said ion exchange resin with said liquid solution, then
    (d) washing said exchange resin to remove impurities, then
    (e) soaking said resin in an eluting solution for at least about 15 minutes then
    (f) eluting said L-lysine from said resin with an eluting solution to form a solution containing recovered L-lysine and then
    (g) concentrating the eluate from step (d) such that the concentration of L-lysine free base is between about 500 and 775 g/L.

* * * * *